US009901718B2

(12) United States Patent
Li et al.

(10) Patent No.: US 9,901,718 B2
(45) Date of Patent: Feb. 27, 2018

(54) BALLOON PRESSURE PUMP

(75) Inventors: Chun Li, Beijing (CN); Yunxing Liu, Beijing (CN)

(73) Assignee: BEIJING DBT MEDI-TECH DEVELOPMENT CO., LTD., Beijing (CN)

( * ) Notice: Subject to any disclaimer, the term of this patent is extended or adjusted under 35 U.S.C. 154(b) by 443 days.

(21) Appl. No.: 14/124,607

(22) PCT Filed: Jun. 6, 2012

(86) PCT No.: PCT/CN2012/076506
§ 371 (c)(1),
(2), (4) Date: Apr. 11, 2014

(87) PCT Pub. No.: WO2012/167723
PCT Pub. Date: Dec. 13, 2012

(65) Prior Publication Data
US 2014/0301867 A1 Oct. 9, 2014

(30) Foreign Application Priority Data
Jun. 8, 2011 (CN) .......................... 2011 1 0151763

(51) Int. Cl.
*A61M 25/10* (2013.01)
*F04B 45/02* (2006.01)
(52) U.S. Cl.
CPC .. *A61M 25/10181* (2013.11); *A61M 25/1018* (2013.01); *A61M 25/10188* (2013.11); *F04B 45/02* (2013.01)
(58) Field of Classification Search
CPC ............... F04B 45/02; A61M 25/1018; A61M 2005/3115; A61M 2005/202; A61M 25/10181; A61M 25/10188
See application file for complete search history.

(56) References Cited

U.S. PATENT DOCUMENTS 4,832,692 A * 5/1989 Box .................. A61M 25/1018
604/210
4,838,864 A 6/1989 Peterson
(Continued)

FOREIGN PATENT DOCUMENTS

| CN | 201232619 Y | 5/2009 |
| CN | 101785902 A | 7/2010 |

(Continued)

OTHER PUBLICATIONS

International Search Report for Application No. PCT/CN 2012/076506, dated Aug. 27, 2012.

*Primary Examiner* — Logan Kraft
(74) *Attorney, Agent, or Firm* — Jenkins, Wilson, Taylor & Hunt, P.A.

(57) ABSTRACT

A balloon pressure pump comprising a cavity (1) having a distal end and a proximal end; a push rod (2) having a distal end and a proximal end, and provided with an external thread and inserted into the cavity; a handle (3) fixedly connected with the proximal end of the push rod (2); a locking member (4) having a distal end and a proximal end and arranged on the proximal end of the push rod (2) and used to lock same; the distal end of the locking member (4) is fixedly connected with the proximal end of the cavity (1). The handle (3) is internally provided with a sleeve (5) to accommodate the push rod (2); said sleeve (5) is fixedly connected with the proximal end of the locking member (4). The proximal end of the push rod (2) includes a spring (11) which is enclosed within the sleeve. The simple structure of the pump simplifies operations such as pressure application, pressure relief, negative pressure evacuation and the like, and is greatly convenient for a user.

6 Claims, 4 Drawing Sheets

(56) References Cited

U.S. PATENT DOCUMENTS

| | | | | |
|---|---|---|---|---|
| 5,052,752 | A | * | 10/1991 | Robinson ............... B60N 2/233 297/362.14 |
| 5,458,571 | A | * | 10/1995 | Lampropoulos ......... G01D 9/00 604/100.03 |
| 5,634,910 | A | * | 6/1997 | Kanner ........... A61M 25/10182 604/208 |
| 7,278,985 | B2 | * | 10/2007 | Ågerup ............. A61M 5/14216 604/181 |
| 7,390,314 | B2 | * | 6/2008 | Stutz, Jr. ............. A61M 5/1456 604/155 |
| 7,629,526 | B1 | * | 12/2009 | Miyajima ............... G10D 13/06 84/422.1 |
| 7,892,202 | B2 | | 2/2011 | Lampropoulos et al. |
| 2014/0301867 | A1 | | 10/2014 | Li et al. |
| 2015/0202369 | A1 | * | 7/2015 | Melander ................ A61M 5/20 604/211 |

FOREIGN PATENT DOCUMENTS

| | | |
|---|---|---|
| CN | 102015004 A | 4/2011 |
| CN | 102218191 A | 10/2011 |
| CN | 202105305 U | 11/2012 |
| EP | 0962231 A1 | 12/1999 |

\* cited by examiner

BALLOON PRESSURE PUMP

TECHNICAL FIELD

The invention relates to a medical device, and more particularly to a balloon pressure pump.

TECHNICAL BACKGROUND

For cardiac intervenient surgeries, a balloon pressure pump is an important device. The balloon pressure pump can be used in angiostenosis surgery and cardiovascular jam surgery by the steps of expanding the balloon, inspecting the pressure in the balloon and shrinking the balloon. Generally, the method of using the balloon pressure pump includes the following steps: amounting a bracket on a balloon catheter; sending the bracket to the disease part in the vessel by the balloon catheter; injecting a diluted contrast agent by a pressure pump for expanding the balloon; bracing the bracket for boarding the angiostenosis in the disease part; pulling back the pressure pump handle back after the bracket is braced; releasing the pressure in the balloon so as to form a negative pressure environment and to separate the balloon and the bracket; withdrawing the balloon catheter for leaving the bracket in the disease part permanently, so as to expanding the angiostenosis.

However, in operating process of the known balloon pressure pumps, the steps of pressurizing, releasing pressure and forming the negative pressure are not convenient.

SUMMARY

For substantially obviating the inconvenience in using, the present invention provides a balloon pressure pump.

The balloon pressure pump provided in the present invention includes:

a cavity having a cavity distal end and a cavity proximal end; a push rod having a push rod distal end and a push rod proximal end; wherein said push rod has external threads and is capable of being inserted to the interior of said cavity; a handle fixed to the push rod proximal end; a locking member having a locking member distal end and a locking member proximal end, wherein the locking member is capable of being fixed to the cavity proximal end and is used for locking the push rod, and wherein the locking member distal end is capable of being fixed to the cavity proximal end; a sleeve provided within the handle and used for receiving the rod, wherein the sleeve is capable of being fixed to the locking member proximal end; a spring provided on the push rod proximal end and enclosed within the sleeve.

The locking member is provided with a through hole and screws, and wherein the screws are capable of engaging with screws provided on the push rod.

The balloon pressure pump further comprises a bottom provided on the locking member and used for locking the rod, wherein the rod is locked as the button is lifted up, and wherein the rod is released as the button is pressed down.

A first pressure pipe outlet and a second pressure pipe outlet are provided on the cavity distal end, wherein a high pressure pipe of the first pressure pipe outlet is connected to a pressure displaying device, and a high pressure pipe of the second pressure pipe outlet connected to a balloon catheter to be inserted into a patient.

The pressure displaying device further includes: a pressure sensor used for inspecting a pressure signal in the balloon pressure pump and/or in the balloon catheter and for converting the pressure signal into an electrical signal; a display unit used for receiving the electrical signal and for showing a pressure data based on the electrical signal.

Accordingly, the balloon pressure pump according to the present invention provides a simple structure can implement and simplify the steps of pressurizing, releasing pressure, forming the negative pressure and so on. Thereby, the balloon pressure pump according to this invention can provide great convenience to the operators.

BRIEF DESCRIPTION OF THE DRAWINGS

The present invention will become more fully understood from the detailed description given herein below for illustration only, and thus are not limitative of the present invention, and wherein.

| Symbol Description | | | |
|---|---|---|---|
| cavity | 1 | push rod | 2 |
| handle | 3 | locking member | 4 |
| button | 41 | button spring | 42 |
| split nut | 43 | sealing-ring seat | 6 |
| sleeve | 5 | O-shape ring | 8 |
| clip ring | 7 | second pressure pipe outlet | 10 |
| first pressure pipe outlet | 9 | balloon catheter | 13 |
| spring | 11 | display unit | 122 |
| pressure displaying device | 12 | | |
| pressure sensor | 121 | | |

DETAILED DESCRIPTION

To further clarify the aspects, the opinions and the advantages of the present invention, a more particular description of this invention will be rendered by reference to specific embodiments thereof which are illustrated in the appended drawings.

According to the embodiment of the present invention, the present invention provides a balloon pressure pump.

Figure 1:
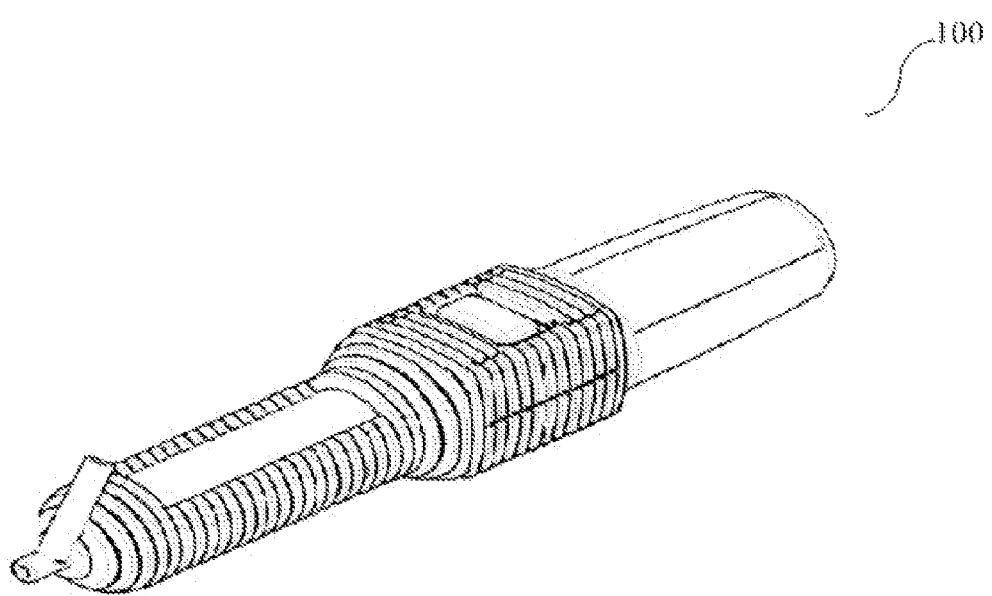
FIG. 1 is a structural view showing the balloon pressure pump in accordance with the first embodiment of the present invention.
Figure 2:
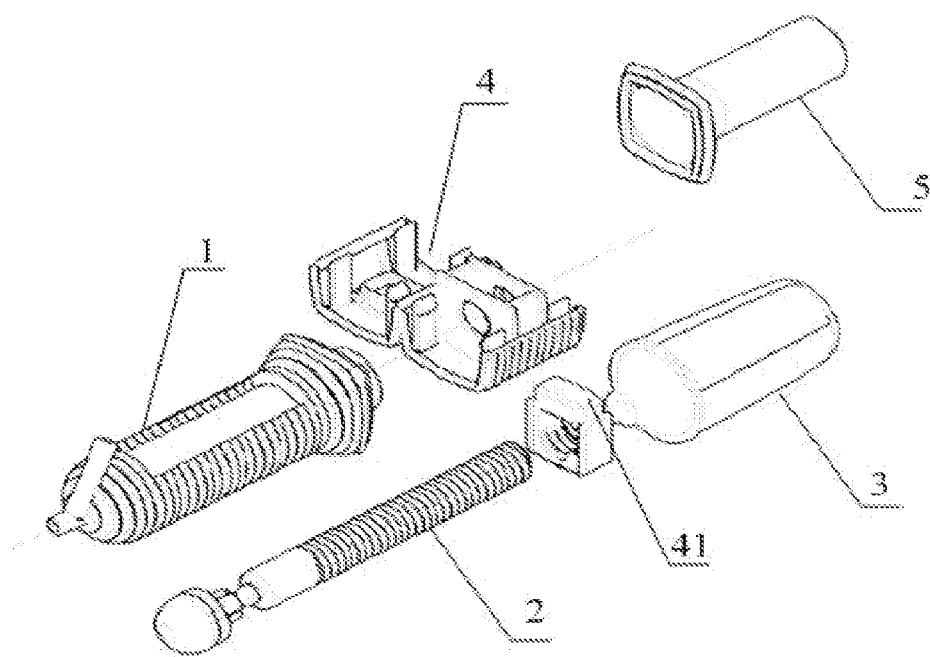
FIG. 2 is an exploded view showing the balloon pressure pump in accordance with the second embodiment of the present invention.

Hereinafter, the present invention will be described with reference to FIGS. 1-2, wherein FIG. 1 is a structural view showing the balloon pressure pump in accordance with an embodiment of the present invention, and FIG. 2 is an exploded view showing the balloon pressure pump in accordance with an embodiment of the present invention. For the sake of brief description with reference to the drawings, the same or equivalent components will be provided with the same reference numbers.

As shown in FIG. 1 and FIG. 2, a balloon pressure pump 100 mainly includes a cavity 1, a push rod 2, a handle 3, a locking member 4 and a sleeve 5, and the detailed description is given hereinafter.

The cavity 1 has a cylinder body, and the interior of the cavity has a hollow structure used to receive medicinal liquids. The cavity 1 includes a distal end having a joint connected to a high pressure pipe, and a proximal end having an opening structure. The push rod 2 is capable of being inserted to the inner of the cavity 1 through the proximal end thereof. Generally, the upper portion of the cavity 1 is transparent for observing the medicinal liquid received in the cavity 1, and graduations can be marked on the cavity 1 for measuring the volume of the medicinal liquid.

The push rod 2 includes a distal end and a proximal end. Meanwhile, the push rod 2 is provided with an external thread. Here, the distal end of the push rod 2 is capable of being inserted into the cavity 1 through the proximal end thereof The distal end of the push rod 2 is connected to a sealing-ring seat (not shown). Wherein, the peripheral sealing surface of the sealing-ring seat contacts with the inner surface of the cavity 1 in a sliding manner and a removable sealing structure is formed accordingly.

The handle 3 has a cylinder structure with hollow interior, and the interior is capable of receiving the sleeve 5. Here, the handle 3 is fixed to the proximal end of the push rod 2. As the handle 3 moves backwards and forwards, the push rod 2 is capable of being moved backwards and forwards together with a handle 3. Furthermore, as the handle 3 is rotated, the push rod 2 is capable of being rotated together with the handle 3. For example, when the handle 3 is rotated clockwise, the rod 2 is capable of being moved forward (towards the distal end) correspondingly. In some embodiments, the appearance of the handle 3 can be designed for convenient operation, for example, some ribs can be provided on the handle 3 for increasing friction.

The locking member 4 includes a locking member distal end and a proximal end. Wherein, the locking member 4 is provided at the proximal end of the push rod 2. In this case, the distal end of the locking member 4 is capable of being fixed to the proximal end of the cavity 1, and the proximal end of the locking member 4 is capable of being fixed to the sleeve 5. Here, the locking member 4 is used to lock the push rod 2, wherein a through hole is provided in the center section of the locking member 4, thus the push rod 2 is capable of passing through this through hole. The bottom of the locking member 4 is provided with screws capable of engaging with the external threads provided on the push rod 2. Furthermore, a button 41 is provided on the locking member 4 and is used to lock the push rod 2. Therefore, as the button 41 is lifted up, the threads of the push rod 2 engage with the screws provided on the bottom of the sleeve 5, thus the push rod 2 can be locked, in this case, the push rod 2 is capable of moving forwards/backwards in a rotating manner by rotating the handle 3 and is not capable of passing through the through hole of the sleeve 5 freely. While, as the button 41 is pressed down, the push rod 2 is released and is capable of moving forwards/backwards and passing through the through hole provided in the sleeve 5. Please note that, the forward/backward moving and the rotation of the push rod 2 are implemented by operating the handle 3.

The sleeve 5 is provided within the handle 3 and used for receiving the push rod 2. Here, the sleeve 5 is capable of being fixed to the proximal end of the locking member 4. Therefore, as the handle 3 is pulled back, the push rod 2 is capable of being dragged backwards. Thus, the push rod 2 is capable of moving within the sleeve 5.

Figure 3A:
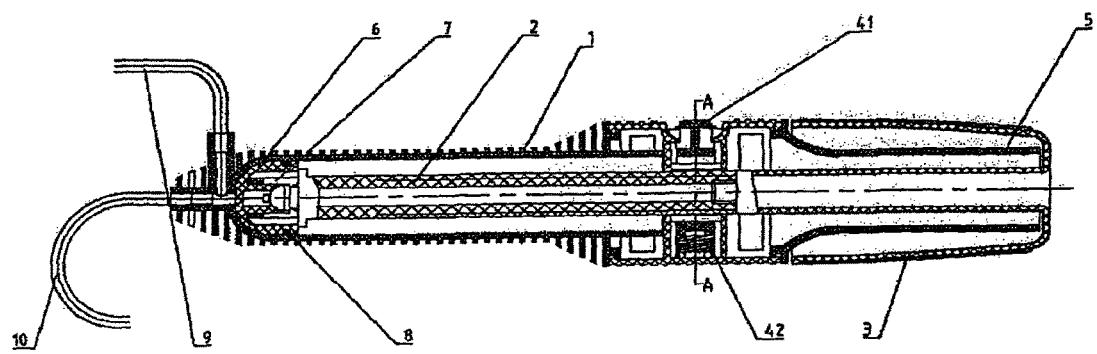
FIG. 3A is an axial section view of the balloon pressure pump provided in the present invention.
Figure 3B:
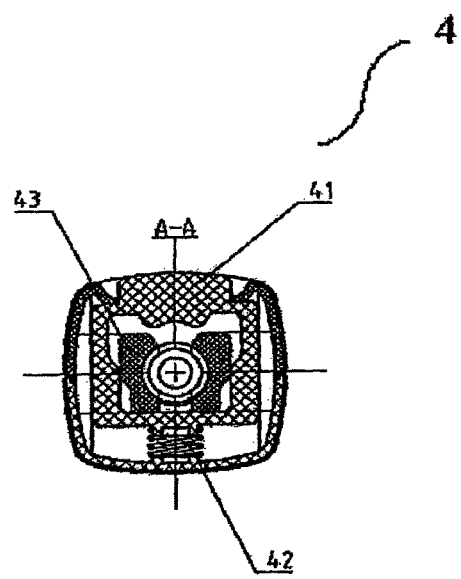
FIG. 3B is an A-A sectional view of the FIG. 3A.

As shown in FIGS. 3A-3B, wherein FIG. 3A is an axial section view of the balloon pressure pump provided in the present invention. As shown in FIG. 3A, the balloon pressure pump includes: the cavity 1, the push rod 2, the handle 3, the locking member 4, the button 41, a split nut 43, the sleeve 5, the sealing-ring seat 6, the clip ring 7, an O-shape ring 8, a first pressure pipe outlet 9 and a second pressure pipe outlet 10.

In FIG. 3A, the same elements shown in FIG. 2 will not be detailed herein. Besides, the clip ring 7 is fixed to the sealing-ring seat 6, thus the clip ring 7 is used to connect the push rod 2 to the sealing-ring seat 6. Here, the distal end of the push rod 2 is configured to have a projecting boss and the clip ring 7 is wedged on the projecting boss, thus the push rod 2 is capable of being pressed to the sealing-ring seat 6. Further, for ensuring a better sealing effect, an O-shape ring 8 can be arranged on the sealing-ring seat 6.

The first pressure pipe outlet 9 and the second pressure pipe outlet 10 can be provided on the distal end of the cavity 1, wherein the high pressure pipe of the first pressure pipe outlet 9 is connected to a pressure displaying device 12, and the high pressure pipe of the second pressure pipe outlet 10 is connected to the balloon catheter 13 to be inserted into a patient's body.

Wherein the pressure displaying device 12 further includes: a pressure sensor 121 used for inspecting a pressure signal in the bump and the balloon catheter, and used for converting the pressure signal into an electrical signal; a display unit 122 used for receiving the electrical signal, showing parameter (including a pressure data, time, pressure curve and so on) based on the electrical signal, and printing the data during the whole process by an external PC.

FIG. 3B is an A-A sectional view of the FIG. 3A. As shown in FIG. 3B, the split nut 43 is provided within the locking member 4 and is used for locking the push rod 2. Furthermore, the button 41 is provided on the upper portion of the locking member 4, and the button spring 42 is provided on the lower portion of the locking member 4. As the button 41 is lifted up, the push rod 2 is locked by the split nut 43, wherein the push rod 2 is merely capable of being rotated respected to the split nut 43 and it cannot move backwards/forwards directly. While, as the button 41 is pressed down, the push rod 2 is capable of being released by the split nut 43 and is capable of moving forwards/backwards directly. Here, the frame can be moved backwards/forwards relative to the push rod 2 under the control of the button 41 and the button spring 42, while the split nut 43 can be used to lock or release the pushrod 2 under the control of the button 41.

In actual operations, when the push rod 2 is pulled backwards, as a negative pressure needs to be produced, the pulling of the push rod 2 is quite inconvenient for the operator. Therefore, according to the embodiment disclosed herein, a spring is provided on the push rod 2, wherein the specific position of the spring is shown in FIG. 4.

Figure 4:
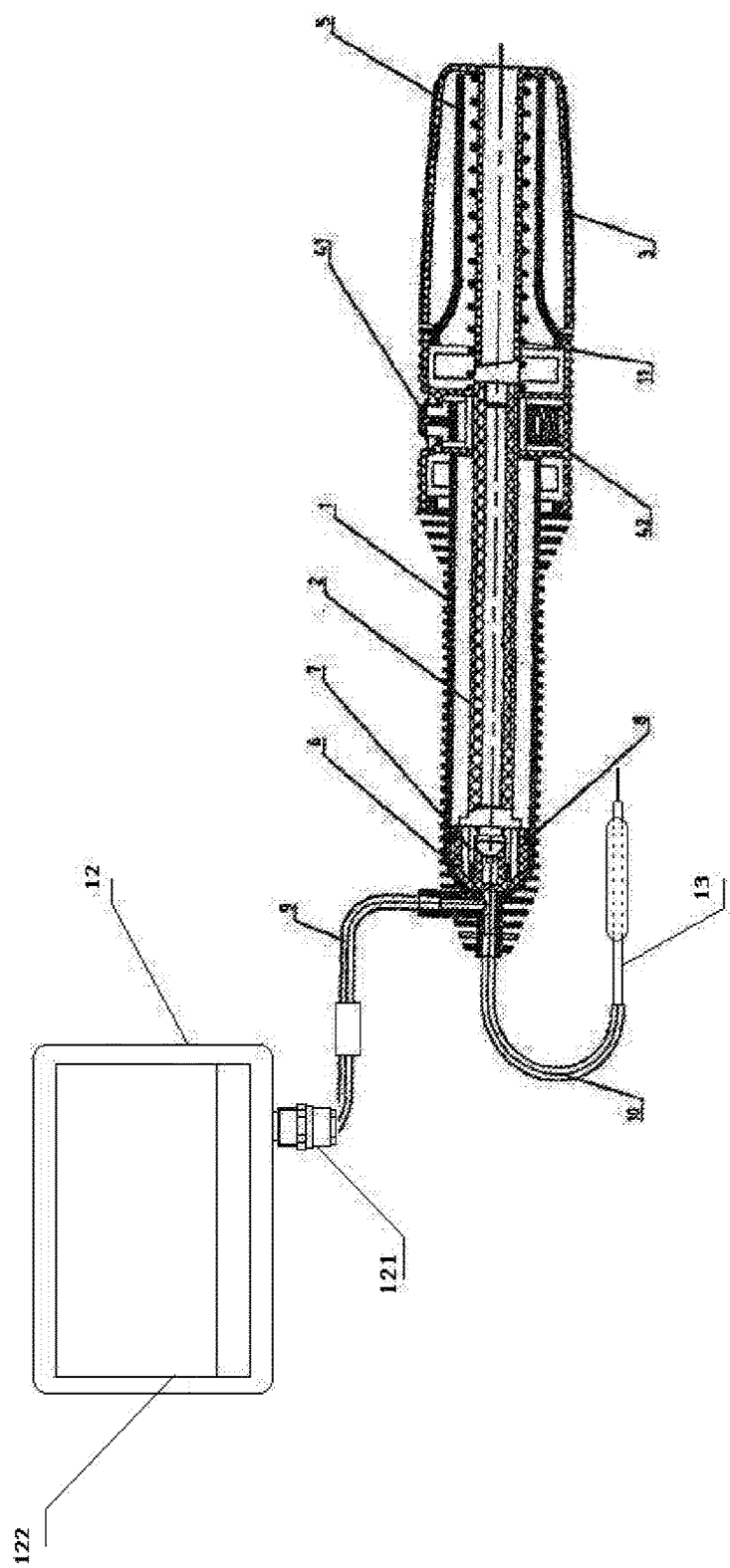
FIG. 4 is an axial section view of the balloon pressure pump according to a preferable embodiment of this invention.

As shown in FIG. 4, according to one embodiment of this invention, a spring 11 is provided on the proximal end of the push rod 2, and the spring 11 can be enclosed within the sleeve 5 by the push rod 2. In practice, the button 41 of the locking member 4 can be pressed down (i.e., the push rod 2 is released) firstly, then the spring 11 drives the handle 3 backward (proximal end), thus the medicinal liquids can be absorbed in the cavity 1. In this case, as a small quantity of air might be absorbed inevitably, the distal end of the cavity 1 is raised upward and the handle is pulled forward to exhaust the air. After that, the balloon catheter connected to the balloon pressure pump is inserted into the patient's body. The button 41 is pressed down and the handle 3 is pulled backward to form a negative pressure, thus the gas and liquid in the balloon catheter are absorbed into the cavity 1. At this time, as the distal end of the cavity 1 is downward, the medicinal liquids can block the gas. The handle 3 is pulled forward (towards the distal end), the button 41 is lifted up for locking the push rod 2 when the handle 3 cannot be pulled any more. In this case, the handle 3 is rotated, for pushing the push rod 2 forward in a rotating manner. At the same time, the sealing-ring seat 6 is moved forward, thus the medicinal liquids can be filled into the balloon catheter. As the pressure in the balloon is increased, the balloon is capable of being expanded and enlarged, and the stent is expanded and shaped. At the same time the spring 11 is depressed. Under the monitoring of the X-ray machine, the button 41 is pressed down again and the push rod 2 is released. The handle 3 is pulled backwards under the effect of the depressed spring 11. The negative pressure is formed in the balloon catheter again, then the liquid within the balloon catheter is drawn off. The balloon is contracted and is isolation from the stent. Thereafter, the catheter is extracted and the stent is implanted.

As described above, the balloon pressure pump according to the present invention provides a simple structure can implement and simplify the steps of pressurizing, releasing pressure, forming the negative pressure and so on. Thereby, the balloon pressure pump according to this invention can provide a great convenience to the operators.

The foregoing embodiment is merely exemplary and is not to be construed as limiting the present invention. It will be apparent to those skilled in the art that various modifications and variations can be made in the present invention without departing from the spirit or scope of the inventions. Thus, it is intended that the present invention covers the modifications and variations of this invention provided they come within the scope of the appended claims and their equivalents.

What is claimed is:

1. A balloon pressure pump for inflating and deflating a catheter, comprising:
    a cavity having a cavity distal end and a cavity proximal end;
    a push rod having a push rod distal end and a push rod proximal end, wherein the push rod has external threads and is capable of being inserted to the interior of the cavity;
    a handle fixed to the push rod proximal end;
    a locking member having a locking member distal end and a locking member proximal end, wherein the locking member is capable of being fixed to the cavity proximal end and is used for locking the push rod, and wherein the locking member distal end is capable of being fixed to the cavity proximal end;
    a sleeve provided within the handle and used for receiving the push rod, wherein the sleeve is capable of being fixed to the locking member proximal end; and
    a spring provided on the push rod proximal end and enclosed within the sleeve,
    wherein the locking member comprises a two-part split nut configured to move linearly along an axis lateral to a longitudinal axis of the push rod, and
    wherein the spring creates a negative pressure in the catheter and retracts the push rod when the locking member is released.

2. The balloon pressure pump according to claim 1, wherein the locking member is provided with a through hole and screws, and wherein the screws are capable of engaging with threads provided on the push rod.

3. The balloon pressure pump according to claim 1, further comprising a button provided on the locking member and used for locking the rod, wherein the rod is locked as the button is lifted up, and wherein the rod is released as the button is pressed down.

4. The balloon pressure pump according to claim 1,
    wherein a first pressure pipe outlet and a second pressure pipe outlet are provided on the cavity distal end, and
    wherein a high pressure pipe of the first pressure pipe outlet is connected to a pressure displaying device, and a high pressure pipe of the second pressure pipe outlet is connected to a balloon catheter that is insertable into a patient body.

5. The balloon pressure pump according to claim 1, wherein the pump is configured for use in cardiovascular stenosis surgery.

6. A balloon pressure pump for inflating and deflating a catheter, comprising:
    a cavity having a cavity distal end and a cavity proximal end;
    a push rod having a push rod distal end and a push rod proximal end, wherein the push rod has external threads and is capable of being inserted to the interior of the cavity;
    a handle fixed to the push rod proximal end;
    a locking member having a locking member distal end and a locking member proximal end, wherein the locking member is capable of being fixed to the cavity proximal end and is used for locking the push rod, and wherein the locking member distal end is capable of being fixed to the cavity proximal end;
    a sleeve provided within the handle and used for receiving the push rod, wherein the sleeve is capable of being fixed to the locking member proximal end; and
    a spring provided on the push rod proximal end,
    wherein the spring is disposed against an interior surface of the handle and enclosed within the sleeve,
    wherein the locking member comprises a two-part split nut configured to move linearly along an axis lateral to a longitudinal axis of the push rod, and
    wherein the spring creates a negative pressure in the catheter and retracts the push rod when the locking member is released.

\* \* \* \* \*